United States Patent [19]

Schermerhorn

[11] Patent Number: 5,257,620
[45] Date of Patent: Nov. 2, 1993

[54] APPARATUS AND METHOD FOR ENDOTRACHEAL INTUBATION

[76] Inventor: Jeffrey W. Schermerhorn, Quarters 4401-E USAFA, Colorado Springs, Colo. 80840

[21] Appl. No.: 806,151

[22] Filed: Dec. 12, 1991

[51] Int. Cl.⁵ .............................................. A61M 25/00
[52] U.S. Cl. .................................. 128/200.26; 604/165
[58] Field of Search ..................... 128/200.26, 207.14, 128/207.15, 207.17, 911, 912, DIG. 26; 604/158, 164, 165

[56] References Cited

U.S. PATENT DOCUMENTS

| | | | |
|---|---|---|---|
| 2,862,498 | 12/1958 | Weekes | |
| 2,912,982 | 11/1959 | Barsky | 128/207.14 |
| 4,244,362 | 1/1981 | Anderson | 128/200.26 |
| 4,304,228 | 12/1981 | Depel | 128/200.26 |
| 4,502,482 | 3/1985 | DeLuccia et al. | 128/207.15 |
| 4,584,998 | 4/1986 | McGrail | 128/604 |
| 4,655,214 | 4/1987 | Linder | 128/207.18 |
| 4,762,125 | 8/1988 | Leiman et al. | 128/207.15 |
| 4,840,173 | 6/1989 | Porter, III | 128/207.15 |
| 4,865,586 | 9/1989 | Hedberg | 128/207.14 X |
| 4,892,095 | 1/1990 | Nakhgevany | 128/207.14 |

Primary Examiner—William H. Grieb
Attorney, Agent, or Firm—Jones & Askew

[57] ABSTRACT

An apparatus for endotracheal intubation comprises a suction stylet telescopically disposed within an endotracheal tube such that the suction stylet is operative to aspirate fluids from the vicinity of the distal end of the endotracheal tube. The apparatus further comprises a connector for releasably axially fixing the suction stylet with respect to the endotracheal tube during intubation. The suction stylet and endotracheal tube are advanced down the trachea simultaneously, the suction stylet aspirating unwanted oral secretions from the operator's field of view during intubation. Once the trachea is intubated, the connector is disconnected and the suction stylet is withdrawn, leaving the endotracheal tube in place.

A method for endotracheal intubation is also disclosed in which a suction stylet is telescopically disposed within an endotracheal tube. The suction stylet and endotracheal tube are advanced simultaneously through the trachea, aspirating unwanted secretions from the operator's field of view during the intubation procedure. Upon completion of intubation, the suction stylet is withdrawn, leaving the endotracheal tube in position.

22 Claims, 6 Drawing Sheets

APPARATUS AND METHOD FOR ENDOTRACHEAL INTUBATION

TECHNICAL FIELD

The present invention relates to a medical device for endotracheal intubation and to a method for performing an endotracheal intubation. More specifically, the invention relates to an endotracheal tube with a suction stylet telescopically disposed therewithin and releasably axially fixed with respect thereto, whereby the endotracheal tube and suction stylet are simultaneously passed into the trachea, the suction stylet clearing unwanted secretions as the endotracheal tube is advanced, and whereby upon completion of intubation the suction stylet may be withdrawn, leaving the endotracheal tube in place.

BACKGROUND OF THE INVENTION

Protecting a patient's airway is the most critical aspect of patient care. The human brain is able to withstand only four minutes of anoxia (lack of oxygen) before suffering irreversible brain damage and, in most cases, death. The preferred method for protecting a patient's airway is to place within the trachea a tube having sufficient rigidity to maintain an open passage between the patient's lungs and the ambient.

In an operating room conditions are ideal for safe, atraumatic endotracheal intubation. The patient is sedated and paralyzed by drugs administered by the anesthesiologist. The position of the patient is ideal. Lighting, equipment, and assistants are also available to help with the intubation. Secretions are controlled with anticholinergic drugs (i.e., agents which decrease oral secretions) and thus do not obstruct visualization of the pathway. The patient is paralyzed by drugs administered prior to the intubation attempts and thus typically does not gag or wretch when a laryngescope blade is inserted down the patient's throat. The patient's stomach is also usually empty in the case of elective surgery, and the possibility of the patient vomiting is thus substantially eliminated.

In emergency medicine, however, a physician, paramedic, or physician assistant is frequently called upon to intubate patients in very undesirable and suboptional working conditions. In an emergency situation, intubation of the trachea is difficult for even the most skilled physician. In the pre-hospital setting, a paramedic is often required to intubate a patient without assistance and in cramped and dark quarters. In an emergency situation, such as cardiopulmonary arrest requiring CPR or a patient who needs intubation while riding in a jostling ambulance, the movement of the patient creates a moving target for the operator. Thus, the circumstances surrounding an emergency intubation greatly complicate the procedure.

The condition of the patient further complicates the emergency endotracheal intubation. When a laryngescope blade is inserted into a semicomatose, non-breathing patient, he or she will frequently wretch, gag, and vomit. Vomitus, oral secretions, and blood must be quickly cleared from the intubator's field of vision and the vocal cords directly visualized to safely and quickly intubate a patient in distress. Improper clearing of secretions increases the risk of aspiration by the patient, and inability to visualize the vocal cords increases the risk of intubation of the esophagus by the operator.

Thus, there is a need for an apparatus which will clear the trachea of unwanted secretions and permit a clear field of view to a physician performing an endotracheal intubation.

To clear the passageway of the presence of oral secretions, vomitus, and blood so that the operator can visualize his reference marks (i.e. the vocal cords) and safely intubate the patient, prior art emergent orotracheal intubation procedures employ a suction device. Typically, the suction device is inserted into the trachea, fluids are aspirated from the field of vision under laryngescopic guidance, the suction device is removed, and an endotracheal tube is inserted. Every second is valuable, and a two step procedure of clearing secretions and then attempting intubation results in lost time. During the time required to suction secretions from the operator's field of vision, remove the suction device, and then grab an endotracheal tube and insert it, the patient may move, or blood, secretions, or vomit may accumulate, obscuring the operator's visualization of the vocal cords.

Thus, there is a need for a method and apparatus which eliminates the delays inherent in prior art procedures whereby the trachea is suctioned with a suction device, the suction device is removed, and an endotracheal tube is subsequently introduced through the trachea.

If an intubation attempt fails, the patient must be preoxygenated and secretions cleared prior to another attempt at intubation. The process of preoxygenating the patient with a bag-mask ventilation device forces air down the trachea as well as down the esophagus into the stomach. When the stomach is distended with air, the patient is more likely to vomit. A distended abdomen also decreases a patient's lung capacity making ventilation more difficult. Further, repeated attempts at intubation causes trauma to the patient, resulting in edema (i.e. swelling) which makes subsequent attempts more difficult. It also increases the chance of aspiration and decreases lung compliance secondary to gastric distention (i.e. filling of the stomach with air).

Thus, there is a need for an apparatus and method which permits secretions to be suctioned from the trachea and intubation to be accomplished accurately, quickly, and consistently on the first attempt so as to obviate the need for repeated preoxygenation and its attendant complications.

SUMMARY OF THE INVENTION

As will be seen, the present invention overcomes these and other problems associated with prior art emergent endotracheal intubation apparatus. Stated generally, the present invention eliminates the lengthy two step process of first suctioning secretions, blood or vomitus and subsequently inserting an endotracheal tube. It combines the clearing of secretions and intubation of the trachea into a single step, thereby permitting intubation to be accomplished accurately, quickly, and consistently on the first attempt.

Stated somewhat more specifically, the present invention comprises an apparatus for performing an endotracheal intubation. The apparatus comprises an endotracheal tube and a suction stylet telescopically received therewithin. The apparatus further comprises a connector means for releasably axially fixing the suction stylet with respect to the endotracheal tube. In this manner the suction stylet and the endotracheal tube may be axially fixed for intubation, the suction stylet being operative to aspirate fluids from the vicinity of the distal end of the endotracheal tube during intubation. Upon completion of intubation the suction stylet may be disconnected from the endotracheal tube and withdrawn therefrom.

In another respect the present invention comprises a suction stylet for use in conjunction with a conventional endotracheal tube for performing an endotracheal intubation. The suction stylet further comprises a connector disposed at the proximal end of the elongated tube for engaging a conventional adapter of the endotracheal tube to releasably axially fix the suction stylet with respect to the endotracheal tube. In this manner the suction stylet and the endotracheal tube may be axially fixed for intubation, the suction stylet being operative to aspirate fluids from the vicinity of the distal end of the endotracheal tube during intubation. Upon completion of intubation the suction stylet may be disconnected from the endotracheal tube and withdrawn therefrom.

In yet another aspect the present invention comprises a method for performing an endotracheal intubation. A suction stylet is positioned within an endotracheal tube such that the suction stylet is operative to aspirate fluids from a location adjacent a distal end of the endotracheal tube. The suction stylet and endotracheal tube are then introduced simultaneously through the trachea of a patient, the suction stylet aspirating fluids and secretions from the trachea as the suction stylet and endotracheal tube are advanced therethrough.

Thus, it is an object of the present invention to provide an improved intubation apparatus and method for emergent endotracheal intubation.

It is another object of the present invention to provide an improved apparatus and method for clearing undesirable secretions from the field of view of an operator during an endotracheal intubation to enhance direct visualization of the vocal cords by the operator and facilitate intubation.

Still another object of the present invention is to provide an apparatus and method which eliminates the delays inherent in prior art procedures whereby the trachea is suctioned with a suction device, the suction device is removed, and an endotracheal tube is subsequently introduced through the trachea.

It is yet another object of the present invention to provide an apparatus and method which permits secretions to be suctioned from the trachea and intubation to be accomplished accurately, quickly, and consistently on the first attempt.

Other objects, features, and advantages of the present invention will become apparent upon reading the following specification, when taken in conjunction with the drawings and the appended claims.

DETAILED DESCRIPTION OF THE DISCLOSED EMBODIMENT

Figure 1:
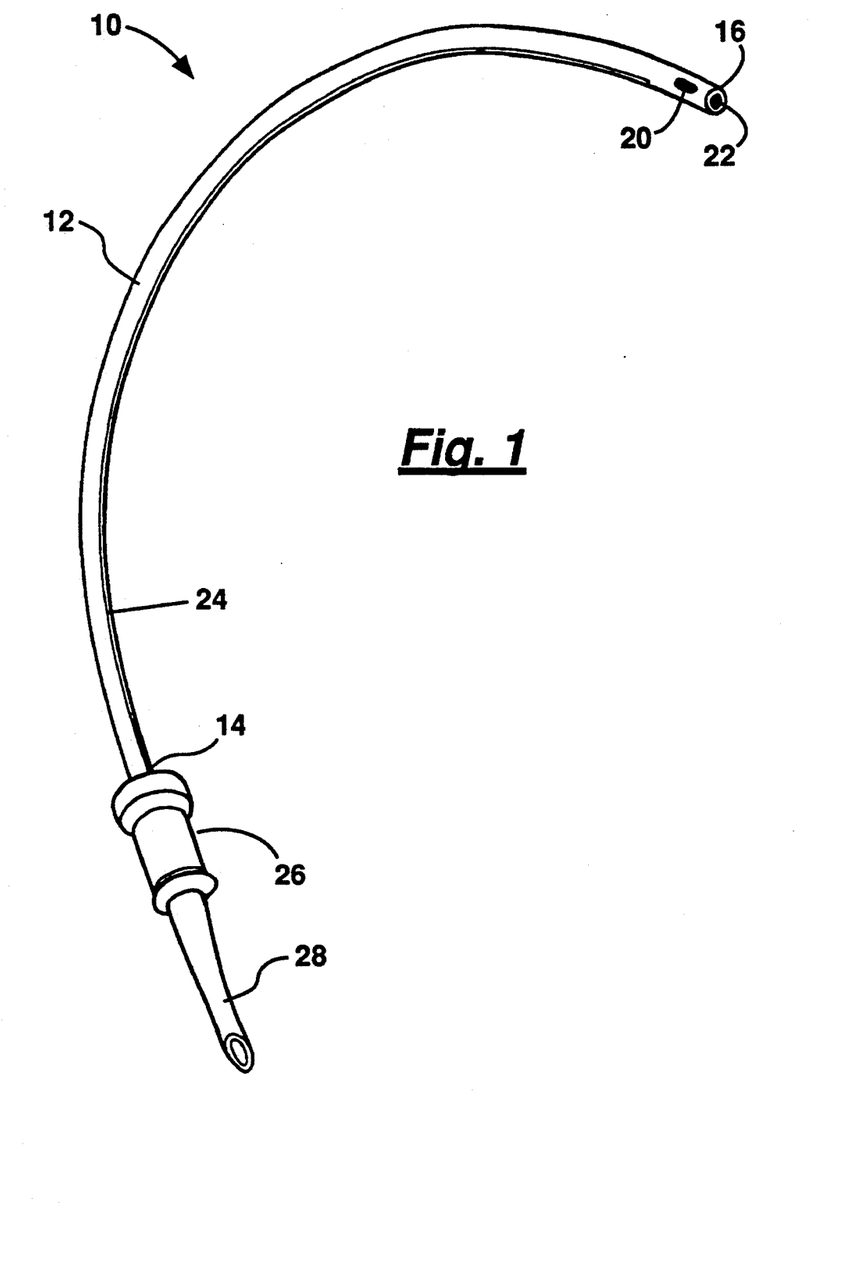
FIG. 1 is a perspective view of a suction stylet according to the present invention.

Referring now to the drawings, in which like numerals indicate like elements throughout the several views, FIG. 1 shows a malleable suction stylet 10 according to the present invention. The suction stylet 10 comprises an elongated tube 12 having a central lumen formed therewithin. The tube 12 has a proximal end 14 and a distal end 16. Lateral and axial orafices 20, 22 are formed at the distal end 16 of the tube 12 in communication with the central lumen and provide a passageway through which unwanted oral secretions can be aspirated from the vicinity of the distal end of the suction stylet 10. A longitudinal wire 24 is implanted within the wall of the elongated tube 12 of the suction stylet 10. The wire 24 is sufficiently malleable to permit the tube 12 to be formed into a desired shape and is sufficiently rigid to permit the tube to retain the desired shape to facilitate passage of the suction stylet 10 through the trachea.

Figure 3A:
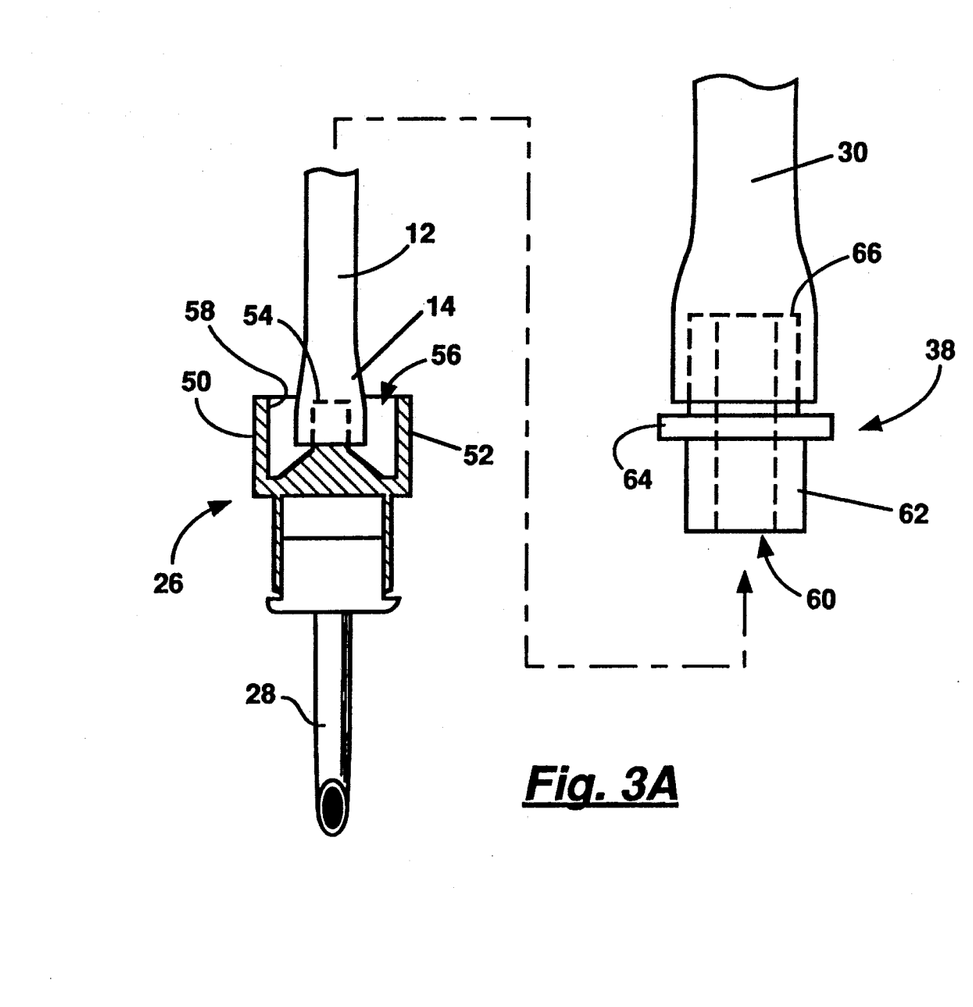
FIG. 3A is an enlarged cross sectional view of a suction stylet connector and mating endotracheal tube connector for axially fixing the suction stylet and endotracheal tube of FIG. 2.
Figure 3B:
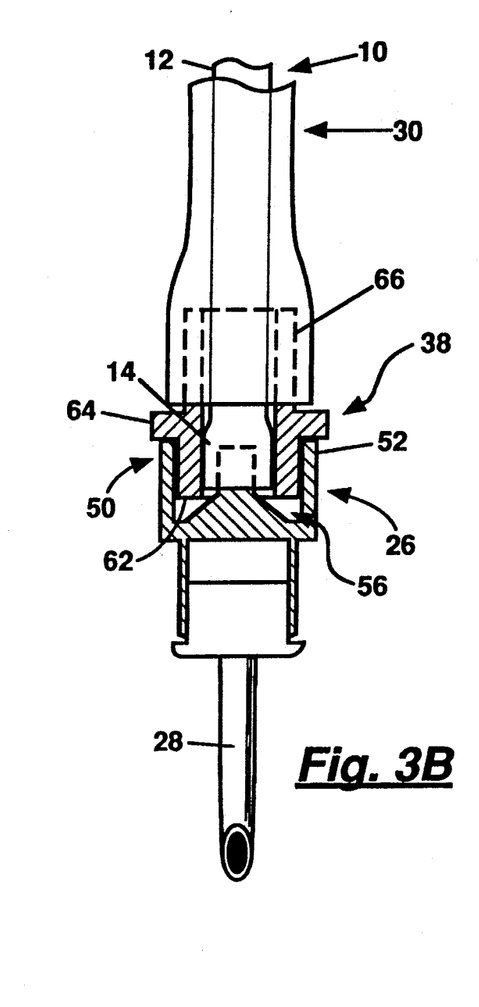
FIG. 3B is an enlarged cross-sectional view showing the suction stylet connector of FIG. 3A matingly engaged with the endotracheal tube connector.

The suction stylet 10 further comprises a suction stylet adaptor 26 coupled to the proximal end 14 of the tube 12. The structure and operation of the suction stylet adapter 26 will be explained below in conjunction with the discussion of FIG. 3. A stem 28 extends from the proximal end of the suction stylet adaptor 26 and provides a means by which the suction stylet 10 can be connected to a conventional suction tube in a manner also to be described below.

Figure 2:
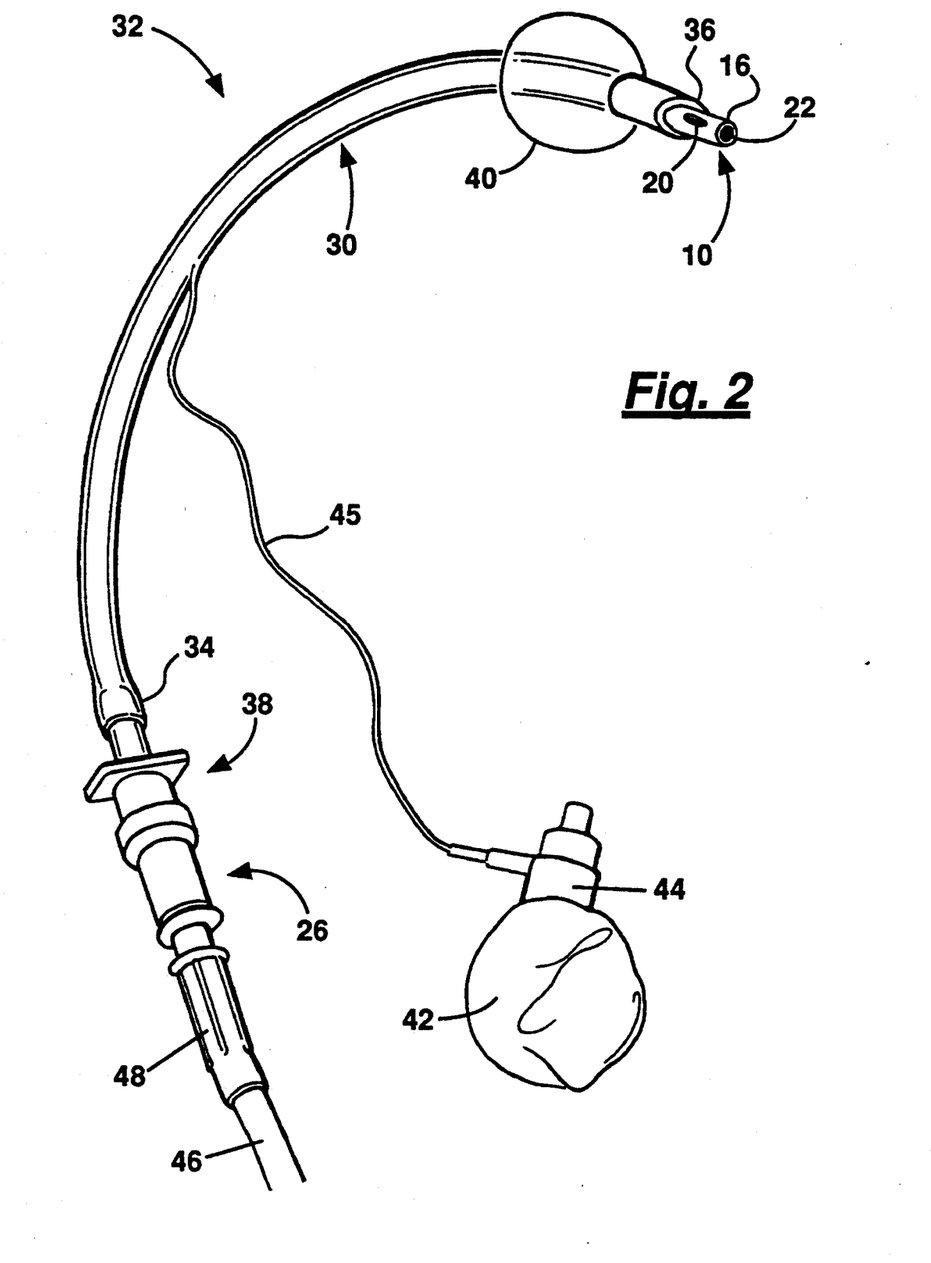
FIG. 2 is a perspective view of the suction stylet of FIG. 1 coaxially disposed within an endotracheal tube.

FIG. 2 shows the suction stylet 10 telescopically disposed within an endotracheal tube 30 to form an assembly 32. The endotracheal tube 30 comprises a proximal end 34 and a distal end 36. An endotracheal tube adapter 38 is located at the proximal end 34 of the endotracheal tube and connects with the suction stylet adapter 26 to fix the suction stylet axially with respect to the endotracheal tube 30. With the suction stylet 10 disposed within the axial lumen of the endotracheal tube 30 and with the endotracheal tube adapter 38 connected to the suction stylet adapter 26, the distal end 16 of the suction stylet extends just beyond the distal end 36 of the endotracheal tube. The orafices 20, 22 of the suction stylet 10 are thus exposed beyond the distal end 36 of endotracheal tube 30.

The endotracheal tube 30 further comprises a balloon 40 of conventional design which is inflated by means of a bladder 42. The bladder 42 includes a one-way valve 44 and is in fluid communication with the balloon 40 by means of a tube 45. These features are well known to those familiar with conventional endotracheal tubes and do not form an essential part of the present invention.

FIG. 2 also shows a suction tube 46 attached to the stem 28 of the suction stylet adapter 26. The suction tube 46 is of conventional design and comprises a friction connector 48 at one end thereof which frictionally engages the stem 28 to couple the suction tube to the proximal end of the suction stylet. The opposite end of the suction tube 46 is connected to a vacuum source in the conventional manner. With the suction tube 46 thus connected to the stem 28 of the suction stylet adapter 26, a vacuum can be created within the central lumen of the suction stylet 10 to effect the aspiration of fluids from the vicinity of the orifices 20, 22 at the distal end 16 of the suction stylet.

FIGS. 3A-B illustrate the structure and function of the suction stylet adapter 26 and endotracheal tube adapter 38. The suction stylet adapter 26 includes an annular collar 50 having upstanding walls 52. A nipple 54 is formed on the suction stylet adapter within the collar 50 and has a diameter slightly larger than the internal diameter of the elongated tube 12. Thus, when the proximal end of the tube 12 is fitted onto the nipple 52, it is retained thereon by a friction fit. With the tube 12 thus mounted onto the nipple 52, an annular space 56 is formed between the inwardly facing surface 58 of the annular collar 50 and the exterior surface of the proximal end of the tube 12.

The endotracheal tube adapter 38 comprises a central axial bore 60 and a downwardly extending annular neck portion 62. The annular neck portion 62 is dimensioned to be received within the annular space 56 defined between the inwardly facing surface 58 of the annular collar 50 and the exterior surface of the proximal end of the tube 12. A transverse flange 64 is formed at the upper end of the neck portion 62, and a nipple 66 extends upwardly from the transverse flange. The nipple 66 is slightly larger than the internal diameter of the endotracheal tube 30 such that when the proximal end 34 of the endotracheal tube is slid onto the nipple 66, the endotracheal tube will be retained thereon by a friction fit.

The assembly of the suction stylet into the endotracheal tube will now be explained with reference to FIGS. 3A-B. The distal end of the suction stylet 10 is directed through the axial bore 60 of the endotracheal tube adapter 38 and through the central lumen of the endotracheal tube. As the distal end of the suction stylet projects beyond the distal end of the endotracheal tube, the endotracheal tube adapter 38 matingly engages the suction stylet adapter 26. The downwardly extending annular neck portion 62 fits into the annular space 56 between the upstanding inner walls 52 of the annular collar 50 and the exterior surface of the proximal end of the tube 12. The outer surface of the neck portion 62 of the endotracheal tube adapter bears against the inner walls 52 of the annular collar 50 of the suction stylet adapter 26. The inner surface of the neck portion 62 frictionally engages the exterior surface of the proximal end 14 of the tube 12 mounted on the nipple 54 of the suction stylet adapter 26. In this manner, the suction stylet 10 is releasably axially fixed within the endotracheal tube 30.

Figure 4:
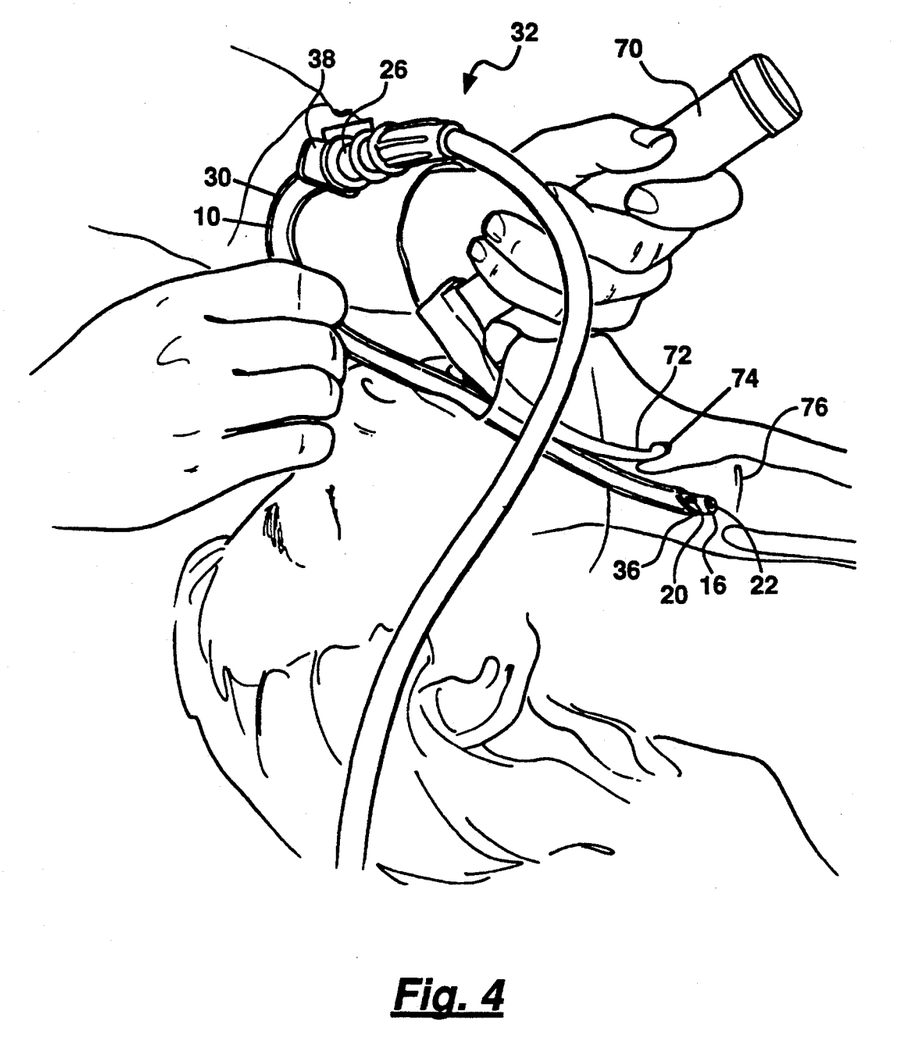
FIG. 4 is a view of an operator intubating a patient using the suction stylet and endotracheal tube of FIG. 3.

FIG. 4 shows the use of the assembly 32 for orotracheally intubating a patient. The suction stylet 10 is shaped into the desired curvature by bending the tube 12 and longitudinal wire 24 implanted therewithin. The suction stylet 10 is malleable and yet has sufficient rigidity that when the stylet is sleeved within the endotracheal tube 30, the endotracheal tube conforms to the configuration of the stylet and maintains the desired configuration throughout the intubation procedure. The suction stylet 10 is then introduced into the endotracheal tube 30, and the suction stylet adapter 26 is frictionally coupled to the endotracheal tube adapter 38 to fix the suction stylet axially with respect to the endotracheal tube.

With the endotracheal tube and suction stylet thus assembled, the operator holds a laryngescope 70 in his left hand. The laryngescope blade 72 is placed into the valecula 74, and the distal end of the assembly 32 is advanced down the trachea. The operator visualizes the vocal cords 76 as secretions are cleared through the suction stylet 10 via orafices 20, 22.

Figure 5:
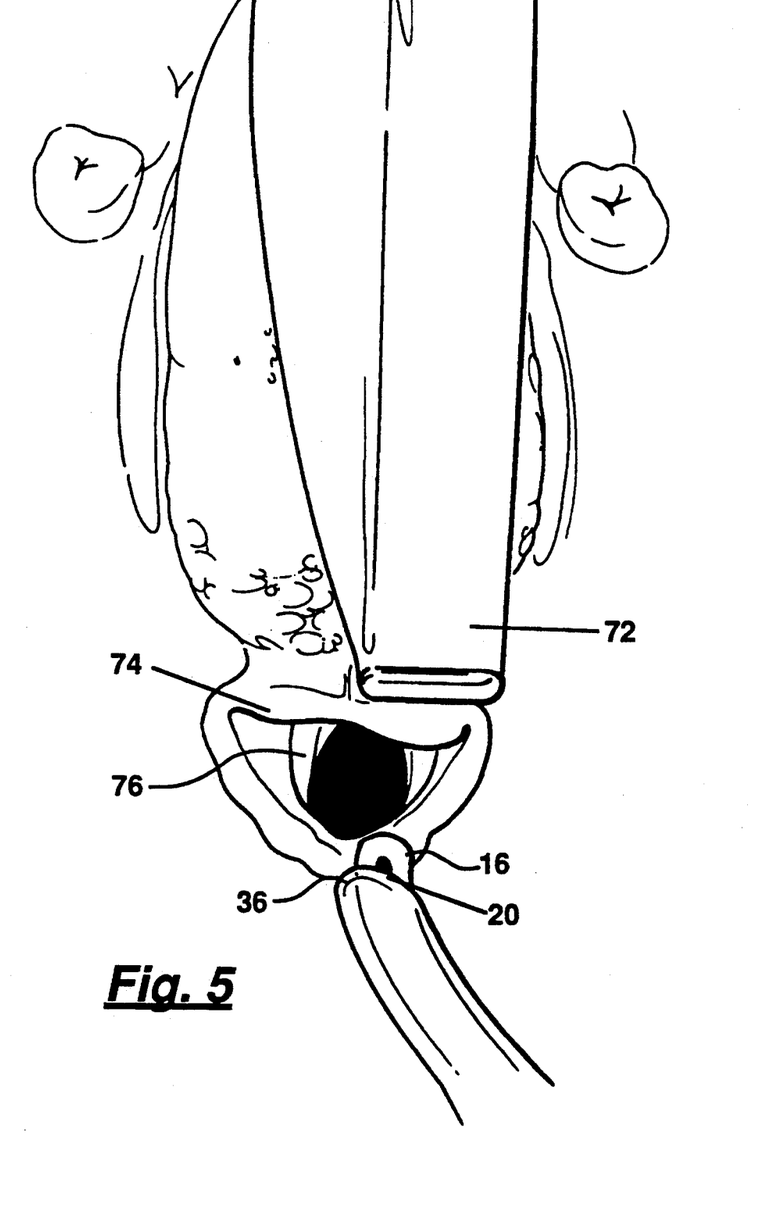
FIG. 5 illustrates the view of the trachea as seen by an operator through a laryngescope during an intubation procedure employing the endotracheal tube and suction stylet assembly of FIG. 3.

FIG. 5 is a view from the intubator's perspective as seen through the laryngescope. The laryngescope blade 72 is shown inserted into the hypopharnynx with its tip placed into the valecular 74. The distal end 16 of the suction stylet 10 and lateral orafice 20 formed therein is shown projecting beyond the distal tip 36 of the endotracheal tube 30. Secretions are cleared from the operator's field of vision as the suction stylet 10 and endotracheal tube 30 are advanced simultaneously through the trachea.

Figure 6:
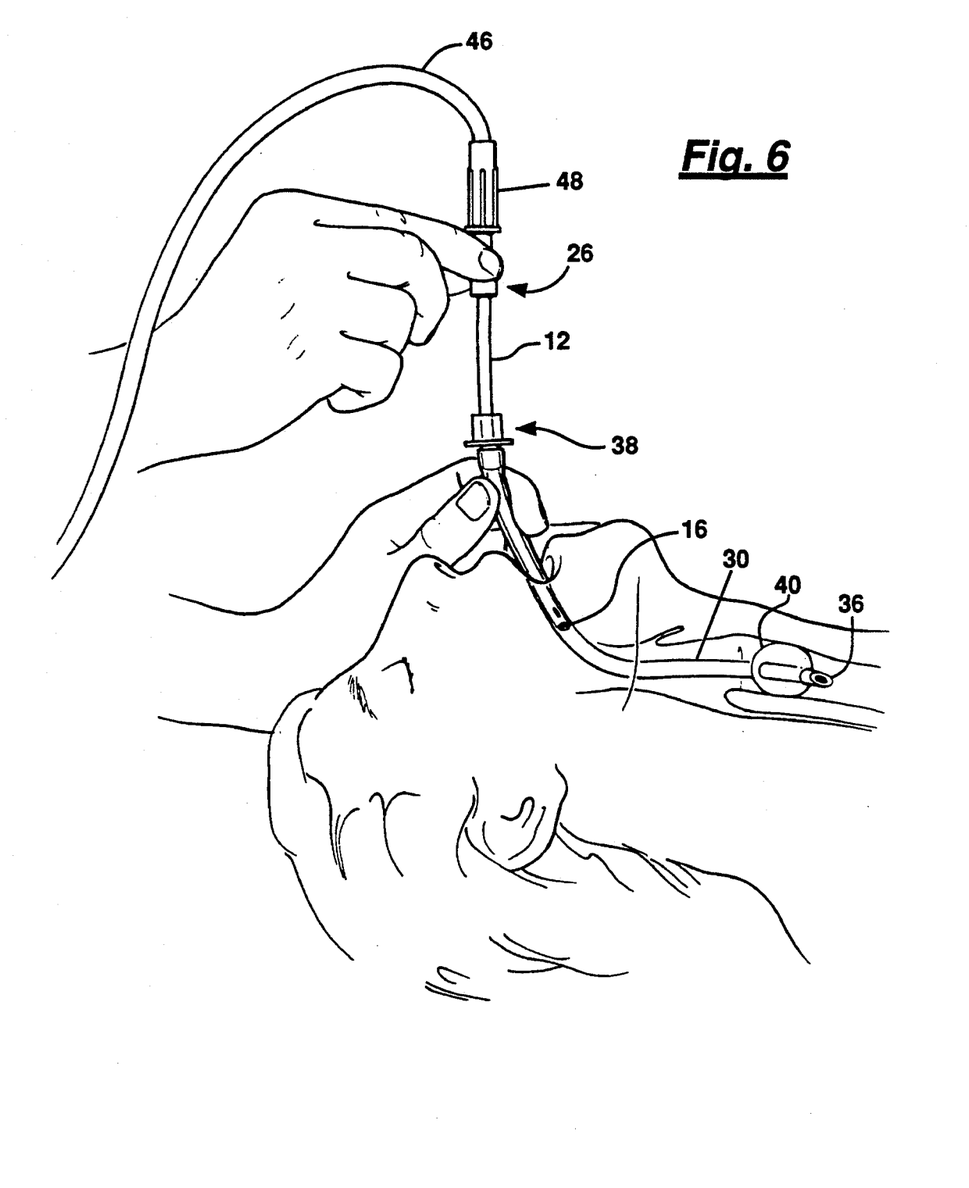
FIG. 6 is a further view of the intubation procedure of FIGS. 4 and 5 showing the endotracheal tube in place in the trachea and the operator removing the suction stylet.

Referring now to FIG. 6, when the endotracheal tube 30 has been advanced to the proper location, the balloon is inflated to anchor the tube within the trachea. The friction connection between the suction stylet adapter 26 and endotracheal tube adapter 38 is then disengaged, and the physician grasps the suction stylet adapter 26 and withdraws the suction stylet 10 from the endotracheal tube 30. With the suction stylet thus removed, the endotracheal tube remains in position in the conventional manner.

It will be appreciated that considerable advantages can be derived from intubating a patient using the suction stylet and endotracheal tube assembly 32 of the present invention. By advancing a suction stylet 10 and endotracheal tube 30 into the trachea simultaneously, unwanted oral secretions are aspirated from operator's field of view as the patient is intubated. Thus, the delay between aspiration and subsequent intubation and the inherent possibility of unwanted secretions reaccumulating and obscuring the operator's field of view are eliminated. Further, when the suction stylet is equipped with the optional longitudinal wire and can be shaped into a desired curvature, the stylet not only performs the function of aspirating fluids but also causes the endotracheal tube to assume an advantageous configuration for intubation. Finally, since aspiration and intubation are combined into a single procedure, intubation can better be carried out under suboptimal conditions and without assistance.

The preferred embodiment has been disclosed with respect to a suction stylet whose distal end extends beyond the distal end of the endotracheal tube during intubation so as to expose the aspiration ports on the end and sides of the suction stylet. However, it will be appreciated that this exact orientation is not necessary and that the suction stylet may be axially disposed relative to the endotracheal tube in any position in which the suction stylet is operative to aspirate fluids from the vicinity of the distal end of the endotracheal tube as intubation is performed. For example, the distal end of the suction stylet may be disposed flush with the distal end of the endotracheal tube or even retracted slightly within the distal end of the endotracheal tube, so long as the suction stylet is still operative to aspirate fluids from the vicinity of the distal end of the endotracheal tube.

While the preferred embodiment has been disclosed with respect to a suction stylet 10 comprising a longitudinal wire 24 implanted therewithin to provide appropriate rigidity and malleability, it will be appreciated that the invention is not limited to a suction stylet having a wire embedded therewithin, and that other means for providing the desired characteristics may be utilized, including forming the suction stylet 10 from a material which exhibits sufficient memory to permit the stylet to be shaped and to retain its configuration once shaped.

Finally, it will be understood that the preferred embodiment has been disclosed by way of example, and that other modifications may occur to those skilled in the art without departing from the scope and spirit of the appended claims.

What is claimed is:

1. An apparatus for performing an endotracheal intubation, comprising:
   an endotracheal tube;
   a suction stylet telescopically disposed within said endotracheal tube; and
   connector means for releasably axially fixing said suction stylet with respect to said endotracheal tube,
   whereby said endotracheal tube and said suction stylet may be simultaneously introduced through the trachea of a patient and said connector means thereafter released such that said suction stylet may be withdrawn from said patient, leaving said endotracheal tube in place within said patient.

2. The apparatus of claim 1, wherein said connector means is fixedly mounted to one of said endotracheal tube and said suction stylet, and wherein said connector means frictionally engages the other of said endotracheal tube and said suction stylet to releasably axially fix said suction stylet with respect to said endotracheal tube.

3. The apparatus of claim 1, wherein said connector means comprises a first connector disposed on said suction stylet and a second connector disposed on said endotracheal tube, said first connector frictionally engaging said second connector to releasably axially fix said suction stylet with respect to said endotracheal tube.

4. The apparatus of claim 1, wherein said suction stylet comprises at least one aspiration orifice formed in a distal end of said suction stylet, and wherein said suction stylet is telescopically disposed within said endotracheal tube such that said distal end of said suction stylet with said aspiration orifice formed therein extends beyond a distal end of said endotracheal tube.

5. The apparatus of claim 1, wherein said connector means releasably axially fixes said suction stylet with respect to said endotracheal tube such that a distal end of said suction stylet is disposed adjacent a distal end of said endotracheal tube.

6. The apparatus of claim 5, wherein said connector means releasably axially fixes said suction stylet with respect to said endotracheal tube such that said distal end of said suction stylet extends beyond said distal end of said endotracheal tube.

7. The apparatus of claim 5, wherein said suction stylet comprises at least one aspiration orifice formed at a distal end of said suction stylet, and wherein said connector means releasably axially fixes said suction stylet with respect to said endotracheal tube such that aspiration orifice formed at said distal end of said suction stylet is disposed exteriorly of said distal end of said endotracheal tube.

8. The apparatus of claim 1, wherein said suction stylet comprises a malleable suction stylet which can be shaped into a desired curvature and which is sufficiently rigid to retain said desired curvature, whereby when said suction stylet is telescopically disposed within said endotracheal tube, said endotracheal tube assumes said desired curvature to facilitate intubation.

9. The apparatus of claim 8, wherein said malleable suction stylet comprises a longitudinal wire embedded within said suction stylet.

10. An apparatus for use with an endotracheal tube for performing an endotracheal intubation, comprising:
    a suction stylet telescopically receivable within said endotracheal tube; and
    connector means operative when said suction stylet is telescopically received within said endotracheal tube for releasably axially fixing said suction stylet with respect to said endotracheal tube,
    whereby said endotracheal tube and said suction stylet can be simultaneously introduced through the trachea of a patient and said connector means thereafter released such that said suction stylet may be withdrawn from said patient, leaving said endotracheal tube in place within said patient.

11. The apparatus of claim 10, wherein said connector means is fixedly mounted to said suction stylet and frictionally engages said endotracheal tube to releasably axially fix said suction stylet with respect to said endotracheal tube.

12. The apparatus of claim 10, wherein said endotracheal tube comprises an endotracheal tube adapter disposed at a proximal end thereof, and wherein said connector means comprises a friction connector disposed on said suction stylet for frictionally engaging said endotracheal tube adapter to releasably axially fix said suction stylet with respect to said endotracheal tube.

13. The apparatus of claim 10, wherein said connector means releasably axially fixes said suction stylet with respect to said endotracheal tube such that a distal end of said suction stylet is disposed adjacent a distal end of said endotracheal tube.

14. The apparatus of claim 13, wherein said connector means releasably axially fixes said suction stylet with respect to said endotracheal tube such that said distal end of said suction stylet extends beyond said distal end of said endotracheal tube.

15. The apparatus of claim 13, wherein said suction stylet comprises at least one aspiration orifice formed at a distal end of said suction stylet, and wherein said connector means releasably axially fixes said suction stylet with respect to said endotracheal tube such that aspiration orifice formed at said distal end of said suction stylet is disposed exteriorly of said distal end of said endotracheal tube.

16. The apparatus of claim 10, wherein said suction stylet comprises a malleable suction stylet which can be shaped into a desired curvature and which is sufficiently rigid to retain said desired curvature, whereby when said suction stylet is telescopically disposed within said endotracheal tube, said endotracheal tube assumes said desired curvature to facilitate intubation.

17. The apparatus of claim 16, wherein said malleable suction stylet comprises a longitudinal wire embedded within said suction stylet.

18. A method for performing an endotracheal intubation, comprising the steps of:
    positioning a suction stylet within an endotracheal tube such that said suction stylet is operative to aspirate fluids from a location adjacent a distal end of said endotracheal tube; and
    introducing said suction stylet and said endotracheal tube simultaneously through the trachea of a patient, said suction stylet being operative to clear said trachea of fluids and secretions as said suction stylet and said endotracheal tube are advanced through said trachea.

19. The method of claim 18, further comprising the step, subsequent to said step of introducing said suction stylet and said endotracheal tube simultaneously through the trachea of a patient, of withdrawing said suction stylet from said patient, leaving said endotracheal tube in place within the trachea of said patient.

20. The method of claim 18, wherein said step of positioning a suction stylet within an endotracheal tube comprises the further step of releasably axially fixing said suction stylet with respect to said endotracheal tube.

21. The method of claim 20, comprising the further steps, subsequent to said step of introducing said suction stylet and said endotracheal tube simultaneously through the trachea of a patient, of axially disengaging said suction stylet from said endotracheal tube and withdrawing said suction stylet from said patient, leaving said endotracheal tube in place within the trachea of said patient.

22. The method of claim 18, wherein said step of positioning a suction stylet within an endotracheal tube comprises the step of positioning a malleable suction stylet within an endotracheal tube, and comprising the further step of forming said malleable suction stylet to a desire shape prior to said step of introducing said suction stylet and said endotracheal tube simultaneously through said trachea so as to facilitate passage of said suction stylet and said endotracheal tube through said trachea.

* * * * *